US011386991B2

(12) United States Patent
Spottiswoode et al.

(10) Patent No.: US 11,386,991 B2
(45) Date of Patent: Jul. 12, 2022

(54) METHODS AND APPARATUS FOR ARTIFICIAL INTELLIGENCE INFORMED RADIOLOGICAL REPORTING AND MODEL REFINEMENT

(71) Applicant: Siemens Medical Solutions USA, Inc., Malvern, PA (US)

(72) Inventors: Bruce S. Spottiswoode, Knoxville, TN (US); Ludovic Sibille, Knoxville, TN (US); Vilim Simcic, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 379 days.

(21) Appl. No.: 16/666,763

(22) Filed: Oct. 29, 2019

(65) Prior Publication Data

US 2021/0125706 A1    Apr. 29, 2021

(51) Int. Cl.

| G16H 30/40 | (2018.01) |
|---|---|
| G16H 15/00 | (2018.01) |
| G06K 9/62 | (2022.01) |
| G06N 20/00 | (2019.01) |
| G06F 3/01 | (2006.01) |
| G06N 3/08 | (2006.01) |
| G06F 40/40 | (2020.01) |

(52) U.S. Cl.
CPC ............. *G16H 30/40* (2018.01); *G06F 3/013* (2013.01); *G06F 3/017* (2013.01); *G06F 40/40* (2020.01); *G06K 9/6268* (2013.01); *G06N 3/08* (2013.01); *G06N 20/00* (2019.01); *G16H 15/00* (2018.01)

(58) Field of Classification Search
CPC ........ G16H 10/60; G16H 20/30; G16H 40/67; G16H 50/20; G16H 50/30; G16H 15/00; G16H 30/40

USPC ......................................................... 382/224
See application file for complete search history.

(56) References Cited

U.S. PATENT DOCUMENTS

| 5,289,374 A | 2/1994 | Doi et al. |
|---|---|---|
| 7,184,582 B2 | 2/2007 | Giger et al. |
| 8,320,651 B2 | 11/2012 | Vining et al. |
| 2008/0062383 A1 | 3/2008 | Endrikhovski et al. |
| 2011/0270123 A1 | 11/2011 | Reiner |
| 2013/0024208 A1 | 1/2013 | Vining |
| 2014/0006926 A1 | 1/2014 | Yeluri et al. |

(Continued)

OTHER PUBLICATIONS

Ganapathi, Tejaswini et al., "A Human Computer Interaction Solution for Radiology Reporting: Evaluation of the Factors of Variation," (2016), pp. 1-18.

*Primary Examiner* — Ajibola A Akinyemi

(57) ABSTRACT

Systems and methods for detecting and classifying clinical features in medical images are disclosed. Natural language processes are applied to speech received from a dictation system to determine clinical and anatomical information for a medical image being viewed. In some examples, gaze location information identifying an eye position is received, as well as an image position for the medical image being viewed. Features of the medical image are detected and classified based on machine learning models. Anatomical associations are generated based on one or more of the classifications, the anatomical information, the gaze information, and the image position. The machine learning models can be trained based on the anatomical associations. In some examples, reports are generated based on the anatomical associations.

20 Claims, 8 Drawing Sheets

(56) References Cited

U.S. PATENT DOCUMENTS

2017/0337329 A1 11/2017 Liu et al.
2018/0003966 A1* 1/2018 Kilcher .................... G02F 1/15
2019/0172580 A1* 6/2019 Boroczky ............ A61B 5/0035

* cited by examiner

| Free text from dictation (302) | Key-value pair translation from NLP (Anatomical terms -> Characterization) (304) | Output from Anatomical Association Algorithm (Ontological Body part / Region / SubRegion -> Characterization) (306) |
|---|---|---|
| "No FDG avidity in the bowel" | Bowel -> Unsuspicious | Abdomen / Small intestine -> Unsuspicious<br>Abdomen / Colon -> Unsuspicious |
| In the Thorax report section: "No lymphadenopathy evident in the thorax" | Thorax, Lymphadenopathy -> Unsuspicious | Thorax / Lymph nodes / All -> Unsuspicious |
| "Intensely FDG avid lesion along right iliac crest" | Right iliac crest -> Suspicious | Pelvis / Ilium / Right -> Suspicious |
| "Moderate FDG uptake extending inferiorly from the left anterolateral aspect of the lower oral cavity" | Oral cavity -> Suspicious | Cranium / Mouth / Floor of mouth -> Suspicious |

FIG. 3

METHODS AND APPARATUS FOR ARTIFICIAL INTELLIGENCE INFORMED RADIOLOGICAL REPORTING AND MODEL REFINEMENT

FIELD

Aspects of the present disclosure relate in general to medical diagnostic systems and, more particularly, to processing images from nuclear imaging systems for diagnostic and reporting purposes.

BACKGROUND

Nuclear imaging systems can employ various technologies to capture images. For example, some nuclear imaging systems employ positron emission tomography (PET) to capture images. PET is a nuclear medicine imaging technique that produces a three-dimensional image representing the distribution of positron emitting isotopes within a body. Some nuclear imaging systems employ computed tomography (CT). CT is an imaging technique that uses rotating x-ray equipment to obtain images, such as of a person's body. In addition, some nuclear imaging systems employ magnetic resonance (MR). MR is an imaging technique that uses magnetic fields to generate images.

Some nuclear imaging systems combine images from PET and CT scanners during an image fusion process to produce images that show information from both a PET scan and a CT scan (e.g., PET/CT systems). Other nuclear imaging systems combine images from PET and MR scanners during an image fusion process to produce images that show information from both a PET scan and an MR scan (e.g., PET/MR systems).

In at least some examples, a clinical expert using dedicated viewing and annotation software to view images produced by these nuclear imaging systems manually annotates medical image features. Some nuclear imaging systems employ artificial intelligence (AI) processes for detecting and classifying clinical features in medical images. These systems, however, can require large volumes of curated, high quality, training data to train the AI processes. The systems can also require large amounts of test and validation data to test and validate the systems. The collection of training, test, and validation data can involve a time consuming and expensive process. These problems can be amplified when attempting to develop AI processes for a wide variety of medical condition diagnosis. These problems can further be amplified when attempting to ensure that the AI processes are robust when implanted with various image scanning devices and settings. As such, there are opportunities to address deficiencies in nuclear imaging systems.

SUMMARY

In some embodiments, a computer-implemented method for training a machine learning model is disclosed. The method includes receiving speech data from a dictation system, converting the received speech data to text, and determining a clinical characterization based on the determined text. In some examples, the text can be determined from a clinical report. The method also includes receiving first image scan data for a first image. For example, the first image scan data can be received from an image scanning device. The method further includes applying a feature extraction process to the received first image scan data to identify at least one feature of the first image. The method also includes applying the machine learning model to the at least one feature of the first image, and determining a first classification of the at least one feature in the first image based on the application of the machine learning model to the at least one feature of the first image. For example, a classifier, such as one based on a convolutional neuronal network, can be applied to the at least one feature of the first image to determine the classification of the at least one feature. The method further includes determining at least one anatomical association for the first image based on the first classification and the clinical characterization. Each anatomical association can identify a body part or body region, and a characterization of that body part or body region, for example. The method also includes training the machine learning model with the at least one anatomical association.

In some embodiments, a computer-implemented method for generating image findings is disclosed. The method includes receiving speech data from a dictation system, and determining a clinical characterization based on the received speech data. The method also includes receiving first image scan data for a first image. The method further includes applying a feature extraction process to the received first image scan data to identify at least one feature of the first image. The method also includes applying a trained machine learning model to the at least one feature of the first image, where the trained machine learning model is trained on historical anatomical associations generated for prior images. The method also includes determining a first classification of the at least one feature in the first image based on the application of the machine learning model to the at least one feature of the first image. Further, the method includes generating at least one anatomical association for the first image based on the first classification and the clinical characterization. The method can also include providing the at least one anatomical association for display.

In some embodiments, a non-transitory computer readable medium stores instructions that, when executed by at least one processor, cause the at least one processor to perform operations comprising receiving speech data from a dictation system, and determining a clinical characterization based on the received speech data. The operations also include receiving first image scan data for a first image. The operations further include applying a feature extraction process to the received first image scan data to identify at least one feature of the first image. The operations also include applying the machine learning model to the at least one feature of the first image, and determining a first classification of the at least one feature in the first image based on the application of the machine learning model to the at least one feature of the first image. The operations further include determining at least one anatomical association for the first image based on the first classification and the clinical characterization. The operations also include training the machine learning model with the at least one anatomical association.

In some embodiments, a non-transitory computer readable medium stores instructions that, when executed by at least one processor, cause the at least one processor to perform operations comprising receiving speech data from a dictation system, and determining a clinical characterization based on the received speech data. The operations also include receiving first image scan data for a first image. The operations further includes applying a feature extraction process to the received first image scan data to identify at least one feature of the first image. The operations also include applying a trained machine learning model to the at least one feature of the first image, where the trained machine learning model is trained on historical anatomical associations generated for prior images. The operations also include determining a first classification of the at least one feature in the first image based on the application of the machine learning model to the at least one feature of the first image. Further, the operations include generating at least one anatomical association for the first image based on the first classification and the clinical characterization. The operations can also include providing the at least one anatomical association for display.

In some embodiments, a system for training a machine learning model is disclosed. The system includes a database and at least one processor communicatively coupled the database. The at least one processor is configured to receive speech data from a dictation system, and determine a clinical characterization based on the received speech data. The at least one processor is also configured to obtain first image scan data for a first image from the database, and apply a feature extraction process to the received first image scan data to identifying at least one feature of the first image. The at least one processor is further configured to apply the machine learning model to the at least one feature of the first image, and determine a first classification of the at least one feature in the first image based on the application of the machine learning model to the at least one feature of the first image. The at least one processor is also configured to generate at least one anatomical association for the first image based on the first classification and the clinical characterization. The at least one processor is further configured to train the machine learning model with the at least one anatomical association.

In some embodiments, a system for generating image findings is disclosed. The system includes a database and at least one processor communicatively coupled the database. The at least one processor is configured to receive speech data from a dictation system, and determine a clinical characterization based on the received speech data. The at least one processor is also configured to obtain first image scan data for a first image from the database, and apply a feature extraction process to the received first image scan data to identifying at least one feature of the first image. The at least one processor is further configured to apply a trained machine learning model to the at least one feature of the first image, where the trained machine learning model is trained on historical anatomical associations generated for prior images. The at least one processor is also configured to determine a first classification of the at least one feature in the first image based on the application of the machine learning model to the at least one feature of the first image. The at least one processor is also configured to generate at least one anatomical association for the first image based on the first classification and the clinical characterization. The at least one processor can also provide the at least one anatomical association for display.

BRIEF DESCRIPTION OF THE DRAWINGS

The following will be apparent from elements of the figures, which are provided for illustrative purposes and are not necessarily drawn to scale.

FIG. 3 illustrates a table with example outputs from the nuclear imaging systems of FIGS. 1 and 2, in accordance with some embodiments.

DETAILED DESCRIPTION

Figure 1:
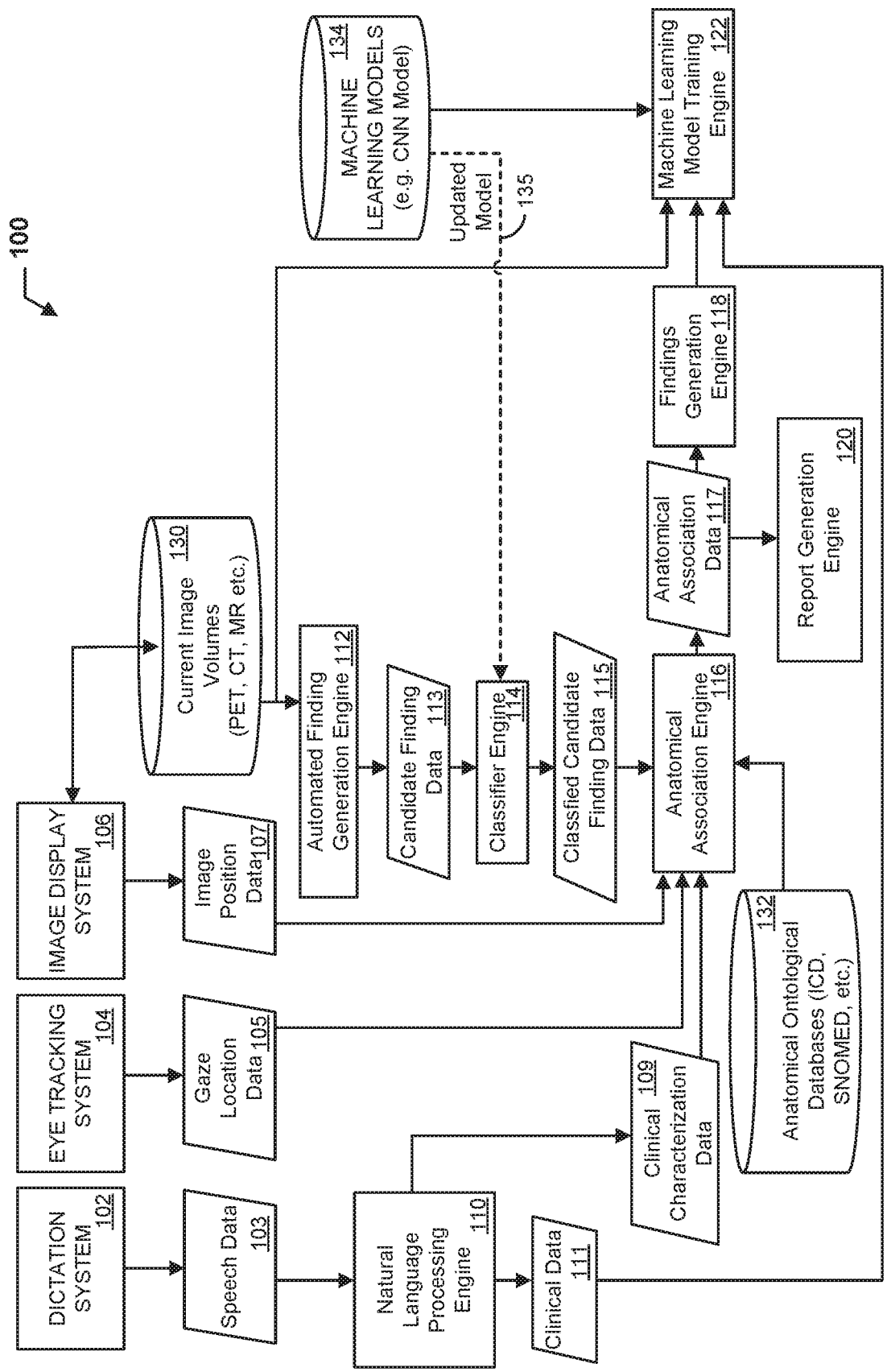
FIG. 1 illustrates a nuclear imaging system, in accordance with some embodiments.

This description of the exemplary embodiments is intended to be read in connection with the accompanying drawings, which are to be considered part of the entire written description.

The exemplary embodiments are described with respect to the claimed systems as well as with respect to the claimed methods. Furthermore, the exemplary embodiments are described with respect to methods and systems for image reconstruction, as well as with respect to methods and systems for training functions used for image reconstruction. Features, advantages or alternative embodiments herein can be assigned to the other claimed objects and vice versa. For example, claims for the providing systems can be improved with features described or claimed in the context of the methods, and vice versa. In addition, the functional features of described or claimed methods are embodied by objective units of a providing system. Similarly, claims for methods and systems for training image reconstruction functions can be improved with features described or claimed in context of the methods and systems for image reconstruction, and vice versa.

Various embodiments of the present disclosure can employ artificial intelligence methods or processes to provide clinical information from nuclear imaging systems. For example, the embodiments can employ artificial intelligence methods or processes to classify features of image data, and generate results for diagnosis. In some embodiments, artificial intelligence methods or processes are trained (e.g., in real-time), to improve the classifications of features in the image data.

In some embodiments, clinical information is gathered during a routine clinical read by way of text from a radiological dictation system, as well as image position from currently viewed planes and infrared eye tracking coordinates. In some examples, clinical information is generated by parsing a clinical report to generate text. The text can be interpreted using natural language processing (NLP) with lexical semantics and relationship extraction to create key-value pairs that identify terms describing base anatomical location and disease characterization.

In some embodiments, candidate findings (e.g. PET threshold-based segmentation) are automatically generated based on images taken by a scanning device. The candidate findings are employed to provide a prediction of the anatomical location (e.g., using a reference atlas or otherwise), and/or an indication of whether the finding is relevant (e.g., suspicious or unsuspicious).

Among various advantages, the embodiments can automatically generate image findings with clinical annotations during a routine clinical read. The embodiments can also retrospectively generate image findings with clinical annotations from image data with accompanying clinical reports. The embodiments can allow for the annotation of measurements at a high anatomical granularity, for the providing of clinical staging support, and/or the generation of structured reports. In some examples, the embodiments allow an Artificial Intelligence (AI) process, such as one or more AI algorithms, that are employed to generate image findings to be trained and improved. For example, the embodiments can associate natural language processing (NLP) results from a radiological report with the output of a convolutional neuronal network (CNN) classifier, and use these associations to improve automated finding generation and to refine the CNN classifier. In some examples, prior study (e.g., scan) results are incorporated to improve the performance of the AI process. Persons of ordinary skill in the art can recognize additional advantages as well.

FIG. 1 illustrates one embodiment of a nuclear imaging system 100. Nuclear imaging system 100 includes an image display system 106. Image display system 106 can perform scans and generate images for display. For example, image display system 106 can include a PET scanner, an MR scanner, a PET/CT scanner, or a PET/MR scanner. Image display system 106 can include a display whereby a technician (e.g., a radiologist) views the images generated. Image display system 106 can generate image position data 107 identifying a current image position. For example, image display system 106 can allow a technician to view an image from various positions (e.g., angles). Image position data 107 identifies the position of the image as is currently being viewed by the technician. In some examples, image display system 106 stores the generated images in database 130.

Nuclear imaging system 100 can also include an eye tracking system 104. Eye tracking system 104 can track an eye position, such as a point of gaze or the motion of an eye, of a technician viewing images on image display system 106. Eye tracking system 104 can include any suitable technology of tracking the technician's eye position. Eye tracking system 104 can generate gaze location data 104, which identifies the technician's eye position. For example, gaze location data 104 can identify the position of the technician's gaze with respect to the technician's head, or with respect to the display the technician is viewing.

Nuclear image system 100 can also include dictation system 102. Dictation system 102 can receive speech from the technician (e.g., as the technician is viewing images on the display of image display system 106), and generate speech data 103 identifying and characterizing the received speech. For example, dictation system 102 can include a microphone to which the technician speaks in. Dictation system 102 can record the speech, translate the speech into words, and generate speech data 103 identifying and characterizing the words of the speech. In some examples, nuclear image system receives a clinical report (e.g., a document in machine readable format), and parses the clinical report to generate speech data 103 identifying and characterizing the text in the clinical report.

Nuclear imaging system 100 further includes natural language processing (NLP) engine 110, automated finding generation engine 112, classifier engine 114, anatomical association engine 116, findings generation engine 118, report generation engine 120, and machine learning model training engine 122. In some examples, one or more of these engines can be implemented in one or more field-programmable gate arrays (FPGAs), one or more application-specific integrated circuits (ASICs), one or more state machines, digital circuitry, or any other suitable circuitry. In some examples, parts or all of each one of these engines can be implemented in software as executable instructions such that, when executed by one or more processors, cause the one or more processors to perform the respective functions.

In this example, NLP engine 110 receives speech data 103 from dictation system 102. NLP engine 110 can apply one or more natural language processing processes (e.g., algorithms) to portions of speech data 103. Based on the application of these adaptive, statistical, or dynamic natural language processing processes, NLP engine 110 can parse the received text data to identify one or more discrete linguistic elements (e.g., a word, a combination of words, a morpheme, etc.), and to generate contextual information that establishes the meaning or a context of one or more discrete linguistic elements. For example, NLP engine 110 can identify clinical (e.g., medical) information, such as clinical indications, clinical treatments, or any other clinical information from speech data 103. NLP engine 110 can generate clinical data 111 identifying and characterizing the clinical information. NLP engine 110 can provide clinical data 111 to machine learning model training engine 122.

NLP engine 110 can also identify clinical characterizations, such as anatomical characterizations, malignancy characterizations, condition characterizations, measurement characterizations, or any other medical characterizations. NLP engine 110 can generate clinical characterization data 109 identifying the clinical characterizations. Each clinical characterization can identify, for example, a key-value pair associated with a characterization. For example, each "key" can identify an anatomical term (e.g., location, area, or part of the body), and each "value" can identify a characterization of the anatomical term (e.g., a size, a volume, a measurement, a condition, etc.). NLP engine 110 can provide clinical characterization data 109 to anatomical association engine 116.

As an example, FIG. 3 illustrates key-value pairs that NLP engine 110 can generate. FIG. 3 includes three columns. First column 302 identifies example text (e.g., as identified by speech data 103) from dictation system 102. Second column 304 identifies example key-value pairs generated by NLP engine 110. For example, speech data 103 can identify "No FDG avidity in the bowel." Based on this text, NLP engine 110 identifies a key of "bowel" and a value of "unsuspicious." In some examples, each "value" of each key-value pair identifies whether the anatomical term identified by the "key" is suspicious or unsuspicious. In some examples, the value of each key-value pair is determined based on applying machine learning on large numbers of (e.g., manually) annotated image features. Third column 306 of FIG. 3 is described further below.

Referring back to FIG. 1, automated finding generation engine 112 is configured to receive image data corresponding to an image from database 130 and generate candidate findings of the image data. For example, automated finding generation engine 112 can employ one or more feature extraction processes (e.g., algorithms) to identify candidate findings (e.g., features) of the image data. Candidate findings identify areas (e.g., blocks) of an image that can be of interest. For example, candidate findings can identify "elevated areas" of the image (e.g., areas of the image with increased radiotracer uptake, areas of focal uptake, etc.). In some examples, automated finding generation engine 112 obtains image data for an image a physician is currently analyzing (e.g., an image displayed by image display system 106), and applies one or more feature extraction processes to the image to identify candidate findings for the image. Automated finding generation engine 112 can generate candidate finding data 113 identifying and characterizing the candidate findings for an image.

Classifier engine 114 can classify the candidate findings identified and characterized by candidate finding data 113. For example, classifier engine 114 can employ one or more classifier processes (e.g., algorithms) to classify the candidate findings. In some examples, classifier engine 114 applies a convolutional neural network (CNN) to candidate finding data 113 to classify the candidate findings. The classifications generated can be anatomical classifications, medical classifications, malignancy classifications, condition classifications, or any other medical classifications. Classifier engine 114 can generate classified candidate finding data 115 identifying and characterizing the classifications.

Anatomical association engine 116 generates anatomical association data 117 identifying and characterizing anatomical associations based on one or more anatomical association processes (e.g., algorithms). An anatomical association process can be based on, for example, a machine learning process such as a clustering algorithm or unsupervised learning algorithm (e.g., a k-means algorithm, a mixture model, a hierarchical clustering algorithm, etc.), a semi-supervised learning algorithm, or a decision-tree algorithm. Anatomical association engine 116 can generate the anatomical associations based on applying the one or more anatomical association processes to clinical characterization data 109 (e.g., key-value pairs), received from NLP engine 110, and one or more of gaze location data 105 received from eye tracking system 104, image position data 107 received from image display system 106, and classified candidate finding data 115 received from classifier engine 114.

To generate the anatomical associations, anatomical association engine 116 can obtain a listing of candidate anatomical possibilities from one or more anatomical ontological databases 132. For example, anatomical ontological database 132 can identify SNOMED descriptions (e.g., one or more words) or ICD (e.g., ICD-10) descriptions. Based on the application of the one or more anatomical association processes, anatomical association engine 116 can identify (e.g., select) a corresponding description from anatomical ontological databases 132.

For example, and referring back to FIG. 3, third column 306 identifies anatomical associations that can be generated by anatomical association engine 116. For example, each anatomical association can identify one or more of a body part, a body region, a body sub-region, and a corresponding characterization. As an example, corresponding to key-value data identifying "Bowl→Unsuspicious," anatomical association engine 116 can generate anatomical association data 117 identifying "abdomen" as the body part, "small intestine" as the region, and "unsuspicious" as the characterization.

Referring back to FIG. 1, anatomical association engine 116 can determine the corresponding description based on one or more predetermined rules. Anatomical association engine 116 can generate anatomical association data 117 identifying the determined descriptions.

In some examples, anatomical association engine 116 is trained with historical data. The historical data can include historical image data identifying a plurality of images, and speech data 103, gaze location data 105, and image position data 107 corresponding to each image.

Findings generation engine 118 receives anatomical association data 117 from anatomical association engine 116 and parses and formats anatomical association data 117 to provide machine learning model training engine 122. For example, findings generation engine 118 can generate machine learning data based on anatomical association data 117, and provide the machine learning data to machine learning model training engine 122.

Findings generation engine 118 can also parse and format anatomical association data 117 to provide the anatomical associations to report generation engine 120. Report generation engine 120 can generate reports (e.g., structured reports) with the anatomical associations. For example, report generation engine 120 can provide the reports for display. In some examples, findings generation engine 118 provides the reports for staging support (e.g., to determine a stage of a disease).

Machine learning model database 134 can store one or more machine learning models (e.g., executable code for a machine learning model). For example, machine learning model database 134 can store a machine learning model employed by classifier engine 114. Classifier engine 114 can obtain a machine learning model from machine learning model database 134, and execute the model. In one example, machine learning model database 134 stores a CNN model. Classifier engine 114 obtains the CNN model from machine learning model database 134, and executes the CNN model currently employed by classifier engine 114.

Machine learning model training engine 122 is configured to train one or more machine learning models (e.g., machine learning algorithms) based on one or more of anatomical associations received from findings generation engine 118, clinical data 111 received from NLP engine 110, and image data obtained from data base 130. For example, machine learning model training engine 122 can obtain a machine learning model from machine learning model database 134 and train the obtained machine learning model. In some examples, machine learning model training engine 122 trains, in real-time, a machine learning model currently employed by classifier engine 114.

For example, as described above, classifier engine 114 can obtain a machine learning model from machine learning model database 134, and employ the machine learning model to classify candidate findings identified by candidate finding data 113. During operation of nuclear imaging system 100, machine learning model training engine 122 can obtain the same machine learning model from machine learning model database 134, and train, during operation of nuclear imaging system 100 (e.g., in real-time), the machine learning model.

Machine learning model training engine 122 can perform the training of the machine learning model based on training data consisting of one or more of anatomical associations received from findings generation engine 118, clinical data 111 received from NLP engine 110, and image data obtained from database 130. The image data can correspond to a current image being viewed on image display system 106 by a technician (e.g., to which the technician is dictating via dictation system 102 and for which eye tracking system 104 is providing gaze location data 105). In some examples, classifier engine 114 obtains an updated model 135, which has been trained by machine learning model training engine 122, from machine learning models database 134.

Figure 2:
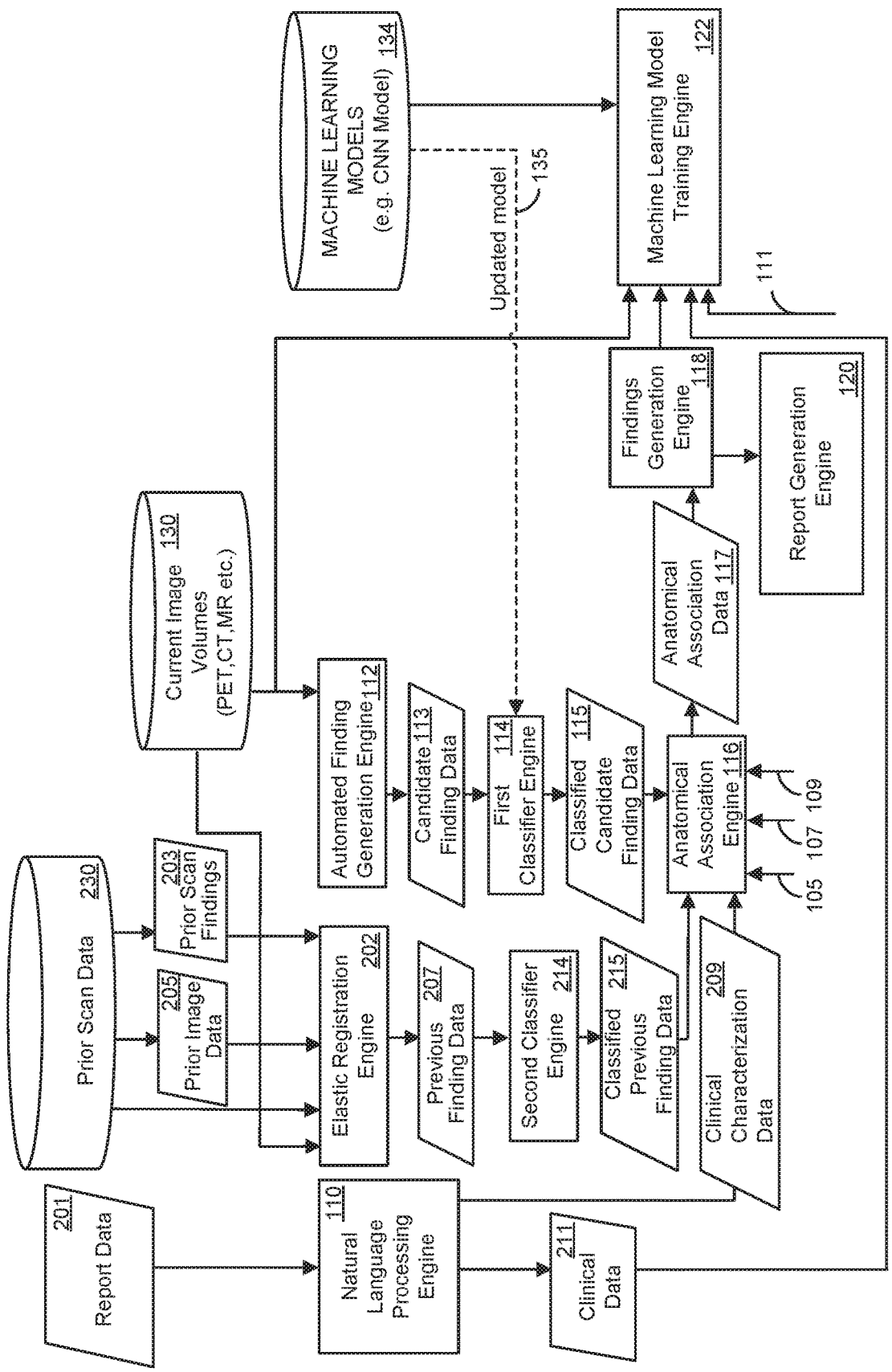
FIG. 2 illustrates another nuclear imaging system, in accordance with some embodiments.

FIG. 2 illustrates a nuclear imaging system 200 that includes portions of nuclear imaging system 100 of FIG. 1.

Nuclear imaging system 200 allows for correspondence between findings across time points. For example, nuclear imaging system 200 allows information from a previous scan (e.g., of a same patient), with accompanying clinical report and image findings, to be integrated to improve the confidence of finding annotations.

As illustrated, nuclear imaging system 200 employs two classifier engines, i.e., first classifier engine 114 and second classifier engine 214, as well as elastic registration engine 202. Nuclear imaging system 200 also includes NLP engine 110, automated finding generation engine 112, anatomical association engine 116, findings generation engine 118, report generation engine 120, and machine learning model training engine 122. In some examples, one or more of these engines can be implemented in one or more field-programmable gate arrays (FPGAs), one or more application-specific integrated circuits (ASICs), one or more state machines, digital circuitry, or any other suitable circuitry. In some examples, parts or all of each one of these engines can be implemented in software as executable instructions such that, when executed by one or more processors, cause the one or more processors to perform the respective functions.

In this example, NLP engine 110 obtains report data 201, which can be report data generated by report generation engine 120 for a prior image scan. NLP engine 110 can obtain report data 201, for example, from prior scan database 230 to which report generation engine 120 stores reports. Report data 201 can identify text from previous reports generated by report generation engine 120, for example.

NLP engine 110 can apply one or more natural language processing processes (e.g., algorithms) to portions of report data 201. Based on the application of these adaptive, statistical, or dynamic natural language processing processes, NLP engine 110 can parse report data 201 to identify one or more discrete linguistic elements (e.g., a word, a combination of words, a morpheme, etc.), and to generate contextual information that establishes the meaning or a context of one or more discrete linguistic elements. For example, NLP engine 110 can identify clinical information, such as clinical indications, clinical treatments, or any other clinical information from report data 201. NLP engine 110 can generate clinical data 211 identifying and characterizing the clinical information. NLP engine 110 can provide clinical data 211 to machine learning model training engine 122.

NLP engine 110 can also identify medical characterizations, such as anatomical characterizations, malignancy characterizations, condition characterizations, measurement characterizations, or any other medical characterizations based on report data 201. NLP engine 110 can generate clinical characterization data 209 identifying the clinical characterizations. Each characterization can identify a key-value pair associated with a characterization. For example, each "key" can identify an anatomical term, and each "value" can identify a characterization of the anatomical term. NLP engine 110 can provide clinical characterization data 209 to anatomical association engine 116.

Elastic registration engine 202 can obtain prior image data 205 identifying an image from a previous scan, and prior scan findings 203 identifying findings, such as anatomical associations, for the previous scan. Prior image data 205 and prior scan findings 203 can be obtained from prior scan database 230. For example, findings generation engine 118 can generate and store prior scan findings 203, identifying anatomical associations for a previous scan, to prior scan database 230. Elastic registration engine 202 can also obtain image data for a current scan from database 130. The current scan can be one, for example, that a technician is currently analyzing. Elastic registration engine 202 can generate previous finding data 207 identifying and characterizing the findings for the previous scan. For example, elastic registration engine 202 can employ well-established technology where deformation fields are derived based on similarity functions that operate on two images (e.g., mutual information).

Second classifier engine 214 can classify the previous findings identified and characterized by previous finding data 207. For example, classifier engine 214 can employ one or more classifier processes (e.g., algorithms) to classify the candidate findings. In some examples, second classifier engine 214 applies a convolutional neural network (CNN) to previous finding data 207 to classify the previous findings. The classifications generated can be anatomical classifications, medical classifications, malignancy classifications, condition classifications, or any other medical classifications. Second classifier engine 214 can generate classified previous finding data 215 identifying and characterizing the classifications.

As described above with respect to FIG. 1, first classifier engine 114 can classify candidate findings identified and characterized by candidate finding data 113. The classifications generated can be anatomical classifications, medical classifications, malignancy classifications, condition classifications, or any other medical classifications. Classifier engine 114 can generate classified candidate finding data 115 identifying and characterizing the classifications.

As described above with respect to FIG. 1, anatomical association engine 116 generates anatomical association data 117 identifying and characterizing anatomical associations based on one or more anatomical association processes (e.g., algorithms). In this example, anatomical association engine 116 receives clinical characterization data 109, gaze location data 105, image position data 107, and classified candidate finding data 115, each corresponding to a same current scan (e.g., a scan a technician is currently viewing on image display system 106). In addition, anatomical association engine 116 receives clinical characterization 209, which identifies medical characterizations for a previous scan, from NLP engine 110. Anatomical association engine 116 also receives classified previous finding data 215, which identifies classifications of findings (e.g., features) for the previous scan, from second classifier engine 214.

Anatomical association engine 116 can generate anatomical associations based on applying the one or more anatomical association processes to one or more of the received data. For example, anatomical association engine 116 can generate anatomical associations based on applying an anatomical association algorithm to one or more of clinical characterization data 109, gaze location data 105, image position data 107, and classified candidate finding data 115, each corresponding to a same current scan, and to one or more of clinical characterization data 209 and classified previous finding data 215, each corresponding to a previous scan (e.g., of a same patient). As such, anatomical association engine 116 can generate anatomical associations based on information from a previous scan (e.g., a scan that was taken weeks or months ago) and information from a current scan, for a patient. Anatomical association engine 116 generates anatomical association data 117 identifying and characterizing the anatomical associations.

In this example, machine learning model training engine 122 can train one or more machine learning models (e.g., obtained from machine learning models database 134) based on data related to a previous scan and a current scan. For example, machine learning model training engine 122 can receive from NLP engine 110 clinical data 111, corresponding to speech data 103 from a dictation for a current scan, and clinical data 211, corresponding to report data 201 from a previous scan. Machine learning model training engine 122 can also receive image data from database 130 for a current scant. In some examples, machine learning model training engine 122 also receives image data for a previous scan, such as from prior scan database 230. Machine learning model training engine 122 can also receive anatomical associations from findings generation engine 118. Machine learning model training engine 122 can train a machine learning model based on one or more of clinical data 111, clinical data 211, image data for a current scan, image data for a previous scan, and the generated anatomical associations.

Figure 4:
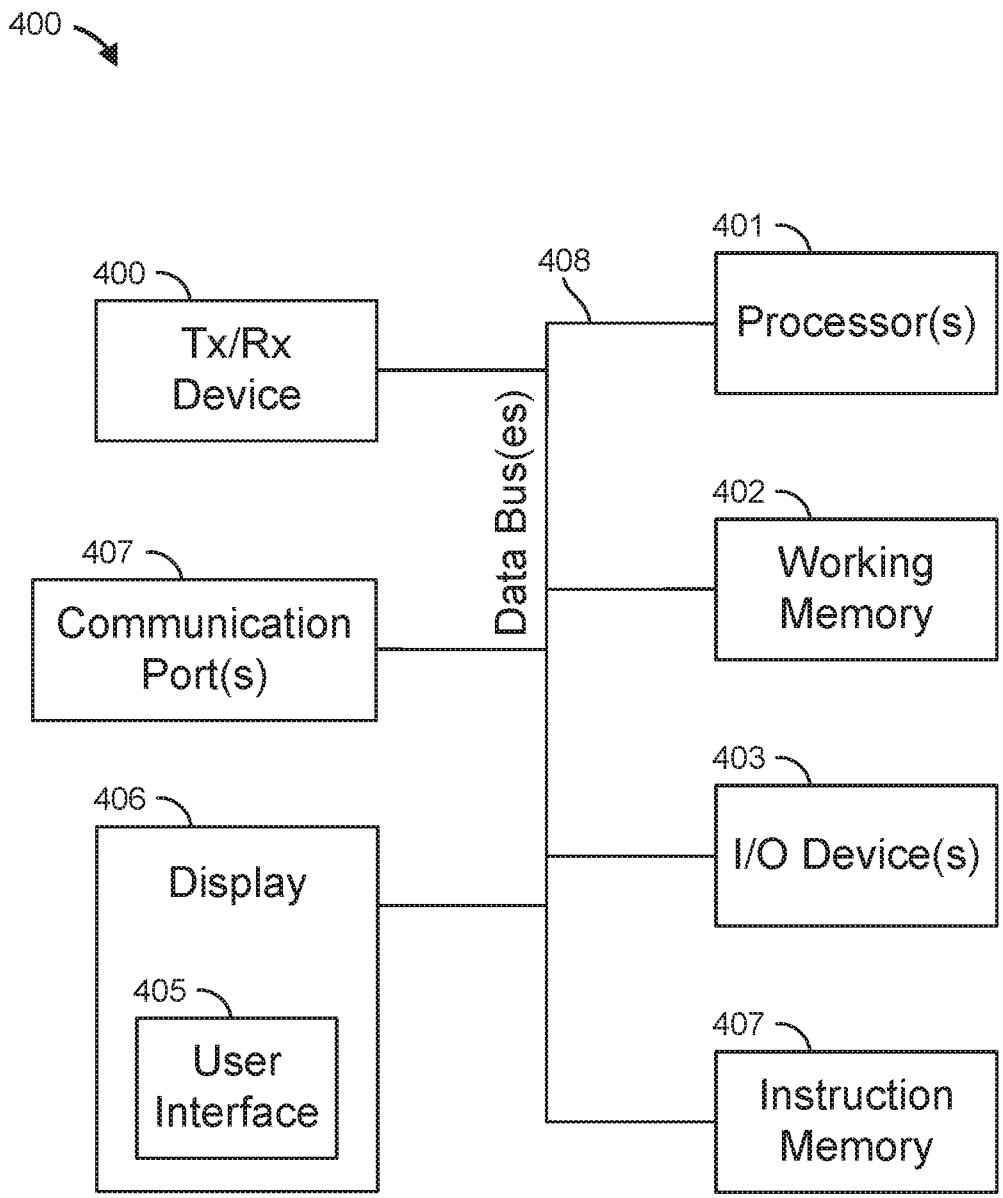
FIG. 4 illustrates a block diagram of an example computing device that can perform one or more functions of the nuclear image systems of FIGS. 1 and 2, in accordance with some embodiments.

FIG. 4 illustrates an anatomical association computing device 400. Anatomical association computing device 400 can implement, for example, one or more of the functions described herein. For example, anatomical association computing device 400 can implement one or more of the functions of NLP engine 110, one or more of the functions of automated finding generation engine 112, one or more of the functions of classifier engines 114, 214, one or more of the functions of anatomical association engine 116, one or more of the functions of findings generation engine 118, one or more of the functions of report generation engine 120, one or more of the functions of elastic registration engine 202, and/or one or more of the functions of machine learning model training engine 122.

Anatomical association computing device 400 can include one or more processors 401, working memory 402, one or more input/output devices 403, instruction memory 407, a transceiver 404, one or more communication ports 407, and a display 406, all operatively coupled to one or more data buses 408. Data buses 408 allow for communication among the various devices. Data buses 408 can include wired, or wireless, communication channels.

Processors 401 can include one or more distinct processors, each having one or more cores. Each of the distinct processors can have the same or different structure. Processors 501 can include one or more central processing units (CPUs), one or more graphics processing units (GPUs), application specific integrated circuits (ASICs), digital signal processors (DSPs), and the like.

Processors 401 can be configured to perform a certain function or operation by executing code, stored on instruction memory 407, embodying the function or operation. For example, processors 401 can be configured to perform one or more of any function, method, or operation disclosed herein.

Instruction memory 407 can store instructions that can be accessed (e.g., read) and executed by processors 401. For example, instruction memory 407 can be a non-transitory, computer-readable storage medium such as a read-only memory (ROM), an electrically erasable programmable read-only memory (EEPROM), flash memory, a removable disk, CD-ROM, any non-volatile memory, or any other suitable memory. For example, instruction memory 407 can store instructions that, when executed by one or more processors 401, cause one or more processors 401 to perform one or more of the functions of classifier engines 114, 214, one or more of the functions of anatomical association engine 116, one or more of the functions of findings generation engine 118, one or more of the functions of report generation engine 120, one or more of the functions of elastic registration engine 202, and/or one or more of the functions of machine learning model training engine 122.

Processors 401 can store data to, and read data from, working memory 402. For example, processors 401 can store a working set of instructions to working memory 402, such as instructions loaded from instruction memory 407. Processors 401 can also use working memory 402 to store dynamic data created during the operation of anatomical association computing device 400. Working memory 402 can be a random access memory (RAM) such as a static random access memory (SRAM) or dynamic random access memory (DRAM), or any other suitable memory.

Input-output devices 403 can include any suitable device that allows for data input or output. For example, input-output devices 403 can include one or more of a keyboard, a touchpad, a mouse, a stylus, a touchscreen, a physical button, a speaker, a microphone, or any other suitable input or output device.

Communication port(s) 407 can include, for example, a serial port such as a universal asynchronous receiver/transmitter (UART) connection, a Universal Serial Bus (USB) connection, or any other suitable communication port or connection. In some examples, communication port(s) 507 allows for the programming of executable instructions in instruction memory 507. In some examples, communication port(s) 407 allow for the transfer (e.g., uploading or downloading) of data, such as PET image data, CT image data, and MR image data.

Display 406 can display user interface 405. User interfaces 405 can enable user interaction with anatomical association computing device 400. For example, user interface 405 can be a user interface for an application that allows for the viewing of images from image display system 106. In some examples, a user can interact with user interface 405 by engaging input-output devices 403. In some examples, display 406 can be a touchscreen, where user interface 405 is displayed on the touchscreen.

Transceiver 404 allows for communication with a network, such as a Wi-Fi network, a cellular network, or any other suitable communication network. For example, if operating in a cellular network, transceiver 404 is configured to allow communications with the cellular network. Processor(s) 401 is operable to receive data from, or send data to, a network via transceiver 404.

Figure 5A:
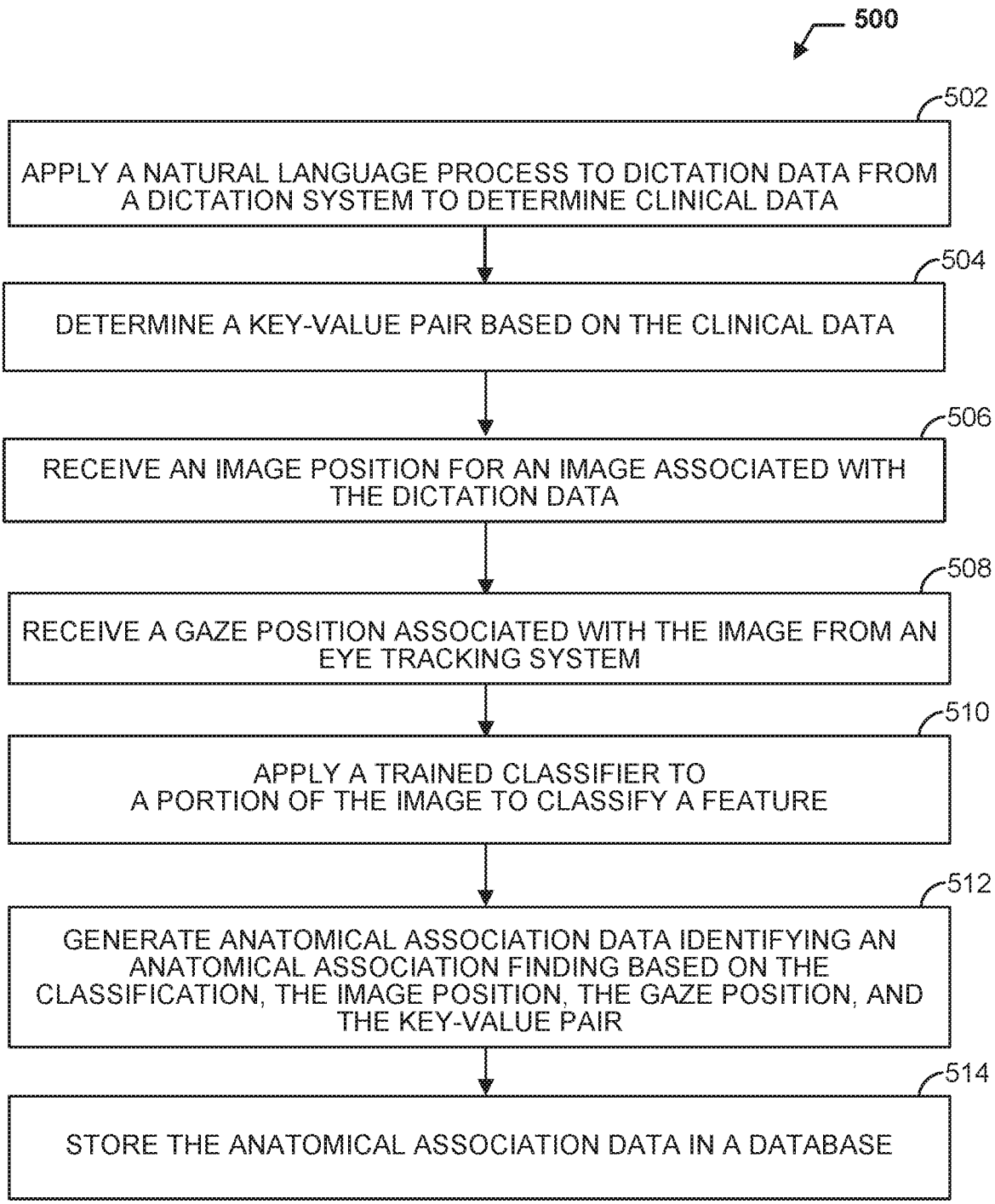
FIGS. 5A and 5B are flowcharts of example methods to provide clinical data, in accordance with some embodiments.

FIG. 5A is a flowchart of an example method 500 that can be carried out by, for example, anatomical association computing device 400. Beginning at step 502, a natural language process is applied to dictation data from a diction system to determine clinical data. For example, NLP engine 110 can apply one or more natural language processes to speech data 103 to determine clinical data 111. At step 504, a key-value pair is determined based on the clinical data. For example, NLP engine 110 can generate clinical characterization data 109 identifying one or more key-value pairs.

Proceeding to step 506, an image position for an image associated with the dictation data is received. For example, anatomical association engine 116 can receive image position data 107 from image display system 107. The image can correspond to an image being displayed by image display system 106. At step 508, a gaze position associated with the image is received from an eye tracking system. For example, anatomical association engine 116 can also receive gaze location data 105 from eye tracking system 104. Gaze location data 105 can identify a gaze location of a technician viewing the image displayed by image display system 106.

At step 510, a trained classifier is applied to a portion of the image to classify a feature. For example, classifier engine 114 can apply a CNN to candidate finding data 113, which identifies features in an image, to classify the features. Proceeding to step 512, anatomical association data is generated. The anatomical association data identifies an anatomical association finding based on the classification generated at step 510, the image position received at step 506, the gaze position received at step 508, and the key-value pair determined at step 504. For example, anatomical association engine 116 can generate anatomical association data 117 identifying and characterizing anatomical associations. At step 514, the anatomical association data is stored in a database, such as prior scan database 230.

Figure 5B:
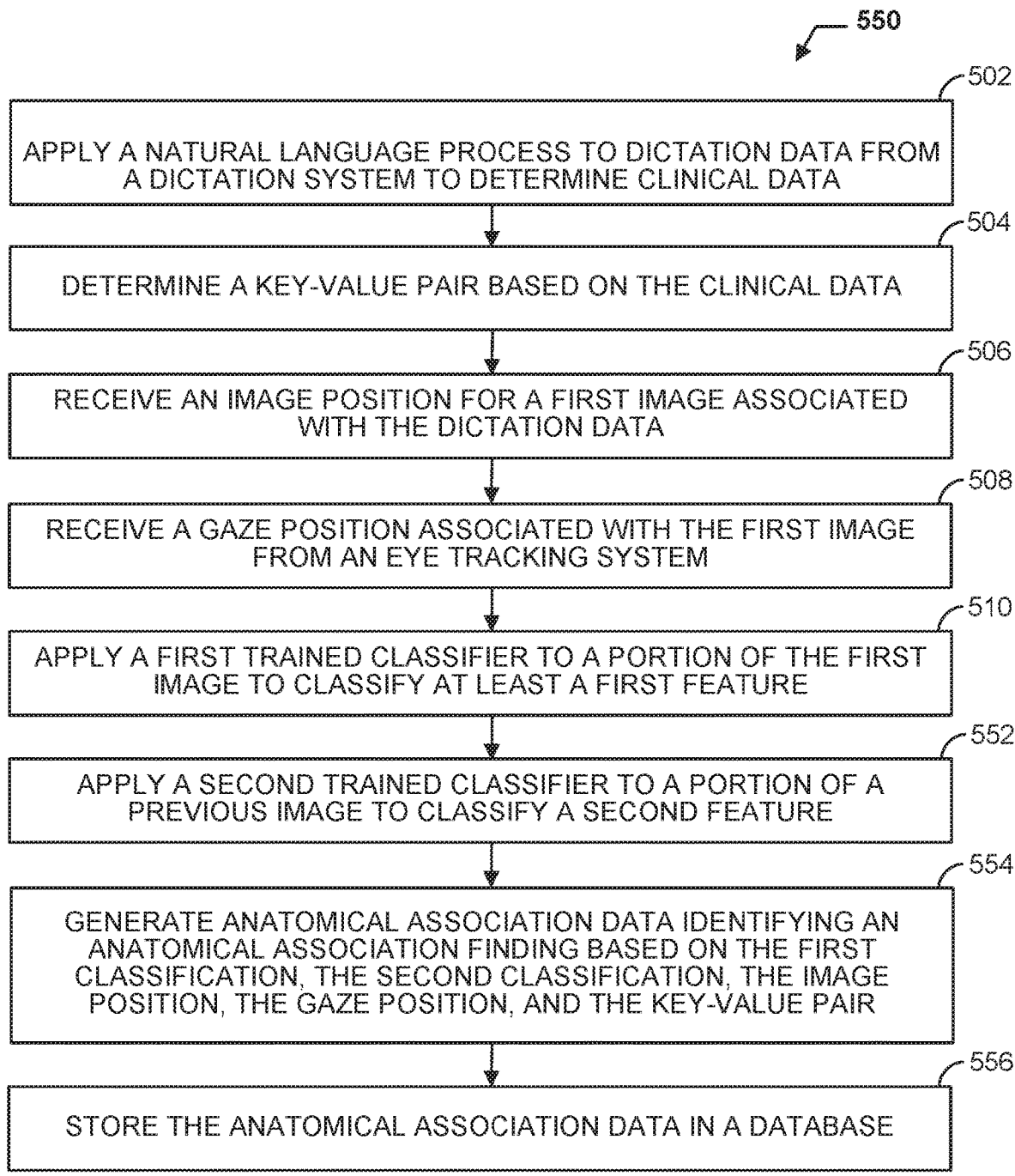

FIG. 5B is another flowchart of an example method 500 that can be carried out by, for example, anatomical association computing device 400. Beginning at step 502, a natural language process is applied to dictation data from a diction system to determine clinical data. At step 504, a key-value pair is determined based on the clinical information. At step 506, an image position for an image associated with the dictation data is received. At step 508, a gaze position associated with the image is received from an eye tracking system. At step 510, a first trained classifier is applied to a portion of the image to classify a feature. For example, classifier engine 114 can apply a CNN to candidate finding data 113, which identifies features in a current image, to classify the features.

Proceeding to step 552, a second trained classifier is applied to a portion of a previous image to classify a second feature. For example, second classifier engine 214 can apply a CNN to previous finding data 207, which identifies features in a previous image, to classify features of the previous image. Continuing to step 554, anatomical association data is generated. The anatomical association data identifies an anatomical association finding based on the classification generated at step 510, the classification generated at step 552, the image position received at step 506, the gaze position received at step 508, and the key-value pair determined at step 504. For example, anatomical association engine 116 can generate anatomical association data 117 identifying and characterizing anatomical associations. At step 556, the anatomical association data is stored in a database, such as prior scan database 230.

Figure 6:
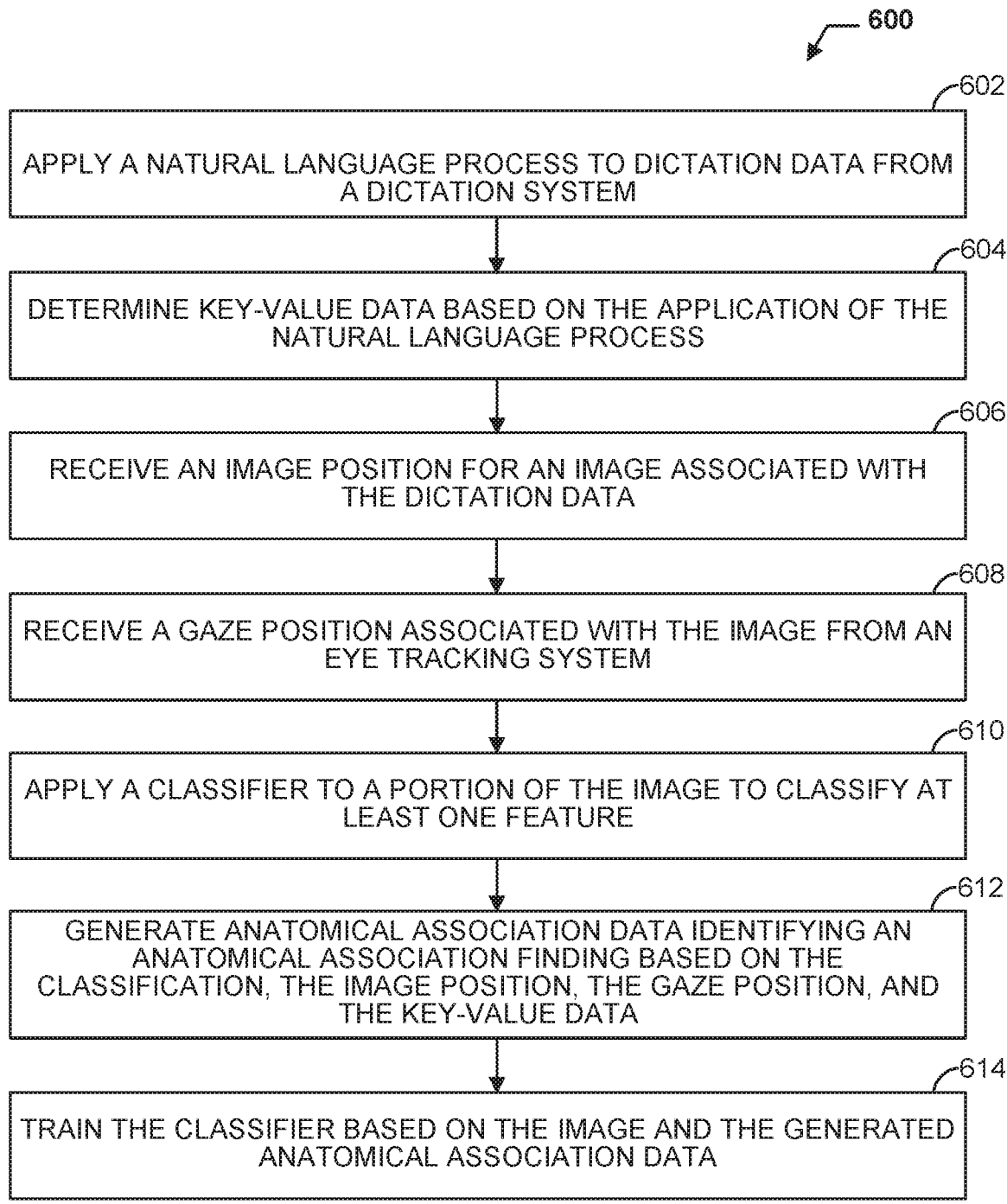
FIG. 6 is a flowchart of an example method to train a machine learning model, in accordance with some embodiments.

FIG. 6 is a flowchart of an example method 700 to train a classifier that can be carried out by, for example, anatomical association computing device 400. Beginning at step 602, a natural language process is applied to dictation data from a dictation system. At step 604, key-value data is determined based on the application of the natural language process to the dictation data. For example, NLP engine 110 can apply one or more natural language processes to speech data 103, and can generate clinical characterization data 109 identifying one or more key-value pairs.

Proceeding to step 606, an image position for an image associated with the dictation data is received. For example, anatomical association engine 116 can receive image position data 107 from image display system 107. The image can correspond to an image being displayed by image display system 106. At step 608, a gaze position associated with the image is received from an eye tracking system. For example, anatomical association engine 116 can also receive gaze location data 105 from eye tracking system 104. Gaze location data 105 can identify a gaze location of a technician viewing the image displayed by image display system 106.

At step 610, a classifier is applied to a portion of the image to classify a feature. For example, classifier engine 114 can apply a CNN to candidate finding data 113, which identifies features in an image, to classify the features. Proceeding to step 612, anatomical association data is generated. The anatomical association data identifies an anatomical association finding based on the classification generated at step 610, the image position received at step 606, the gaze position received at step 608, and the key-value data determined at step 604. For example, anatomical association engine 116 can generate anatomical association data 117 identifying and characterizing anatomical associations as described above with respect to FIGS. 1 and 2.

At step 614, the classifier is trained based on the image and the anatomical association data generated at step 612. For example, machine learning model training engine 122 can train a machine learning model, employed by classifier engine 114, with anatomical association data provided by findings generation engine 118 and image data for a current image. In some examples, the machine learning model is also trained on clinical data determined by NLP engine 110, such as clinical data 111.

Figure 7:
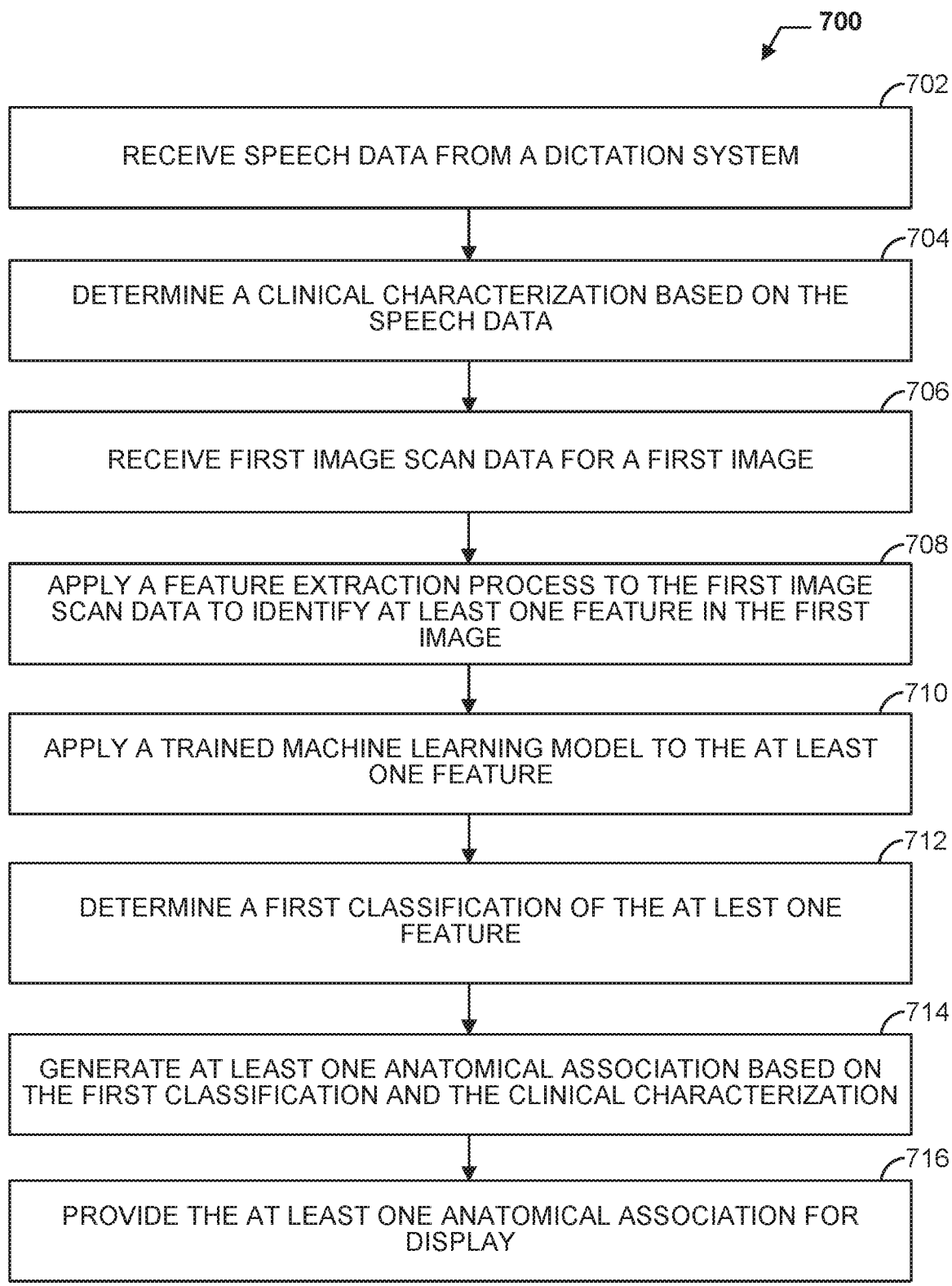
FIG. 7 is a flowchart of another example method to provide clinical data, in accordance with some embodiments.

FIG. 7 is flowchart of an example method 700 that can be carried out by, for example, anatomical association computing device 400. At step 702, speech data from a dictation system is received. At step 704, a clinical characterization is determined based on the received speech data. For example, NLP engine 110 can apply one or more natural language processes to speech data 103, and can generate clinical characterization data 109 identifying one or more key-value pairs.

At step 706, first image scan data for a first image is received. At step 708, a feature extraction process is applied to the received first image scan data to identify at least one feature of the first image. At step 710, a trained machine learning model is applied to the at least one feature of the first image. The trained machine learning model is trained on historical anatomical associations generated for prior images, for example.

Proceeding to step 712, a first classification of the at least one feature in the first image is determined based on the application of the trained machine learning model to the at least one feature of the first image. At step 714, at least one anatomical association for the first image is generated based on the first classification and the clinical characterization. At step 716, the at least one anatomical association is provided for display. For example, the at least one anatomical association may be displayed for evaluation by a physician.

In some examples, a computer-implemented method for training a machine learning model comprises receiving speech data from a dictation system, and determining a clinical characterization based on the received speech data. The method also comprises receiving first image scan data for a first image. The method comprises applying a feature extraction process to the received first image scan data to identify at least one feature of the first image. The method further comprises applying the machine learning model to the at least one feature of the first image. The method also comprises determining a first classification of the at least one feature in the first image based on the application of the machine learning model to the at least one feature of the first image. The method comprises generating at least one anatomical association for the first image based on the first classification and the clinical characterization. The method further comprises training the machine learning model with the at least one anatomical association.

In some examples, the method comprises training the machine learning model with the clinical characterization. In some examples, the method comprises training the machine learning model with the first image scan data. In some examples, determining the clinical characterization comprises applying a natural language process to the received speech data. In some examples, the machine learning model is based on a convolutional neuronal network.

In some examples, the method comprises determining a clinical indication based on the received speech data, wherein generating the at least one anatomical association for the first image is based on the clinical indication. In some examples, determining the clinical indication comprises identifying an anatomical term and a characterization of the anatomical term based on the received speech data.

In some examples, any of the above methods can comprise receiving gaze location data from an eye tracking system, wherein the gaze location data identifies a position of an eye of a technician viewing the first image, and receiving image position data from an image display system, where the image position data identifies a position of the first image being viewed by the technician, and where generating the at least one anatomical association for the first image is based on the gaze location data and the image position data.

In some examples, a computer-implemented method for generating image findings comprises receiving a clinical report, parsing the clinical report for text, and determining a clinical characterization based on the text. The method also comprises receiving first image scan data for a first image. The method further comprises applying a feature extraction process to the received first image scan data to identify at least one feature of the first image. The method also comprises applying a trained machine learning model to the at least one feature of the first image, where the trained machine learning model is trained on historical anatomical associations generated for prior images. The method further comprises determining a first classification of the at least one feature in the first image based on the application of the trained machine learning model to the at least one feature of the first image. The method also comprises generating at least one anatomical association for the first image based on the first classification and the clinical characterization. In some examples, the method comprises providing the at least one anatomical association for display.

In some examples, a computer-implemented method for generating image findings comprises receiving speech data from a dictation system, and determining a clinical characterization based on the received speech data. The method also comprises receiving first image scan data for a first image. The method further comprises applying a feature extraction process to the received first image scan data to identify at least one feature of the first image. The method also comprises applying a trained machine learning model to the at least one feature of the first image, where the trained machine learning model is trained on historical anatomical associations generated for prior images. The method further comprises determining a first classification of the at least one feature in the first image based on the application of the trained machine learning model to the at least one feature of the first image. The method also comprises generating at least one anatomical association for the first image based on the first classification and the clinical characterization. In some examples, the method comprises providing the at least one anatomical association for display.

In some examples, determining the clinical characterization comprises applying a natural language process to the received speech data. In some examples, the trained machine learning model is based on a convolutional neuronal network.

In some examples, the method further comprises generating a report based on the at least one anatomical association for staging support. In some examples, the method further comprises determining a clinical indication based on the received speech data, where generating the at least one anatomical association for the first image is based on the clinical indication.

In some examples, determining the clinical indication comprises identifying an anatomical term and a characterization of the anatomical term based on the received speech data.

In some examples, any of the above methods can comprise receiving gaze location data from an eye tracking system, where the gaze location data identifies a position of an eye of a technician viewing the first image, and receiving image position data from an image display system, where the image position data identifies a position of the first image being viewed by the technician, where generating the at least one anatomical association for the first image is based on the gaze location data and the image position data.

In some examples, generating the at least one anatomical association for the first image comprises obtaining a plurality of candidate anatomical possibilities from a database, and determining the at least one anatomical association based on the plurality of candidate anatomical possibilities.

In some examples, any of the above methods can comprise applying a second trained machine learning model to at least one feature of a second image, and determining a second classification of the at least one feature of the second image based on the application of the second trained machine learning model to the at least one feature of the second image, where generating the at least one anatomical association for the first image is based on the second classification. In some examples the second image is a previously scanned image for a same patient.

In some examples, a non-transitory computer readable medium stores instructions that, when executed by at least one processor, cause the at least one processor to perform operations comprising: receiving speech data from a dictation system; determining a clinical characterization based on the received speech data; receiving first image scan data for a first image; applying a feature extraction process to the received first image scan data to identify at least one feature of the first image; applying a machine learning model to the at least one feature of the first image; determining a first classification of the at least one feature in the first image based on the application of the machine learning model to the at least one feature of the first image; generating at least one anatomical association for the first image based on the first classification and the clinical characterization; and training the machine learning model with the at least one anatomical association.

In some examples, a non-transitory computer readable medium stores instructions that, when executed by at least one processor, cause the at least one processor to perform operations comprising: receiving a clinical report; parsing the clinical report for text; determining a clinical characterization based on the text; receiving first image scan data for a first image; applying a feature extraction process to the received first image scan data to identify at least one feature of the first image; applying a trained machine learning model to the at least one feature of the first image, wherein the trained machine learning model is trained on historical anatomical associations generated for prior images; determining a first classification of the at least one feature in the first image based on the application of the trained machine learning model to the at least one feature of the first image; generating at least one anatomical association for the first image based on the first classification and the clinical characterization; and providing the at least one anatomical association for display.

In some examples, a non-transitory computer readable medium stores instructions that, when executed by at least one processor, cause the at least one processor to perform operations comprising: receiving speech data from a dictation system; determining a clinical characterization based on the received speech data; receiving first image scan data for a first image; applying a feature extraction process to the received first image scan data to identify at least one feature of the first image; applying a trained machine learning model to the at least one feature of the first image, wherein the trained machine learning model is trained on historical anatomical associations generated for prior images; determining a first classification of the at least one feature in the first image based on the application of the trained machine learning model to the at least one feature of the first image; generating at least one anatomical association for the first image based on the first classification and the clinical characterization; and providing the at least one anatomical association for display.

In some examples, the non-transitory computer readable medium stores instructions that, when executed by at least one processor, further cause the at least one processor to perform operations comprising: applying a second trained machine learning model to at least one feature of a second image; and determining a second classification of the at least one feature of the second image based on the application of the second trained machine learning model to the at least one feature of the second image, wherein generating the at least one anatomical association for the first image is based on the second classification. In some examples, the second image is a previously scanned image for a same patient.

In some examples, a system comprises a database and at least one processor communicatively coupled to the database. The at least one process is configured to receive speech data from a dictation system, and determine a clinical characterization based on the received speech data. The at least one processor is also configured to obtain first image scan data for a first image from the database. The at least one processor is configured to apply a feature extraction process to the received first image scan data to identify at least one feature of the first image. The at least one processor is also configured to apply a machine learning model to the at least one feature of the first image. The at least one processor is further configured to determine a first classification of the at least one feature in the first image based on the application of the machine learning model to the at least one feature of the first image. The at least one processor is also configured to generate at least one anatomical association for the first image based on the first classification and the clinical characterization. The at least one processor is further configured to train the machine learning model with the at least one anatomical association.

In some examples, a system comprises a database and at least one processor communicatively coupled to the database. The at least one processor is configured to receive a clinical report, parse the clinical report for text, and determine a clinical characterization based on the text. The at least one processor is also configured to obtain first image scan data for a first image from the database and apply a feature extraction process to the received first image scan data to identify at least one feature of the first image. The at least one processor is also configured to apply a trained machine learning model to the at least one feature of the first image. The trained machine learning model is trained on historical anatomical associations generated for prior images. The at least one processor is also configured to determine a first classification of the at least one feature in the first image based on the application of the trained machine learning model to the at least one feature of the first image. The at least one processor is also configured to generate at least one anatomical association for the first image based on the first classification and the clinical characterization. In some examples, the at least one processor is also configured to provide the at least one anatomical association for display.

In some examples, a system comprises a database and at least one processor communicatively coupled to the database. The at least one processor is configured to receive speech data from a dictation system and determine a clinical characterization based on the received speech data. The at least one processor is also configured to obtain first image scan data for a first image from the database and apply a feature extraction process to the received first image scan data to identify at least one feature of the first image. The at least one processor is also configured to apply a trained machine learning model to the at least one feature of the first image. The trained machine learning model is trained on historical anatomical associations generated for prior images. The at least one processor is also configured to determine a first classification of the at least one feature in the first image based on the application of the trained machine learning model to the at least one feature of the first image. The at least one processor is also configured to generate at least one anatomical association for the first image based on the first classification and the clinical characterization. In some examples, the at least one processor is also configured to provide the at least one anatomical association for display.

In some examples, the at least one processor is configured to receive gaze location data from an eye tracking system, wherein the gaze location data identifies a position of an eye of a technician viewing the first image, and receive image position data from an image display system, where the image position data identifies a position of the first image being viewed by the technician, where generating the at least one anatomical association for the first image is based on the gaze location data and the image position data.

In some examples the at least one processor is configured to apply a second trained machine learning model to at least one feature of a second image, and determine a second classification of the at least one feature of the second image based on the application of the second trained machine learning model to the at least one feature of the second image, where generating the at least one anatomical association for the first image is based on the second classification. In some examples, the second image is a previously scanned image for a same patient.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein can be applied to other embodiments without the use of inventive faculty. The present disclosure is not intended to be limited to the embodiments shown herein, but is to be accorded the widest scope consistent with the principles and novel features disclosed herein.

What is claimed is:

1. A computer-implemented method for generating image findings comprising:
   receiving speech data from a dictation system;
   determining a clinical characterization based on the received speech data;
   receiving first image scan data for a first image;
   applying a feature extraction process to the received first image scan data to identify at least one feature of the first image;
   applying a trained machine learning model to the at least one feature of the first image, wherein the trained machine learning model is trained on historical anatomical associations generated for prior images;
   determining a first classification of the at least one feature in the first image based on the application of the trained machine learning model to the at least one feature of the first image;
   generating at least one anatomical association for the first image based on the first classification and the clinical characterization; and
   providing the at least one anatomical association for display.

2. The computer-implemented method of claim 1 wherein determining the clinical characterization comprises applying a natural language process to the received speech data.

3. The computer-implemented method of claim 1 wherein the trained machine learning model is based on a convolutional neuronal network.

4. The computer-implemented method of claim 1, further comprising generating a report based on the at least one anatomical association for staging support.

5. The computer-implemented method of claim 1, further comprising determining a clinical indication based on the received speech data, wherein generating the at least one anatomical association for the first image is based on the clinical indication.

6. The computer-implemented method of claim 5 wherein determining the clinical indication comprises identifying an anatomical term and a characterization of the anatomical term based on the received speech data.

7. The computer-implemented method of claim 6 further comprising:
   receiving gaze location data from an eye tracking system, wherein the gaze location data identifies a position of an eye of a technician viewing the first image; and
   receiving image position data from an image display system, wherein the image position data identifies a position of the first image being viewed by the technician, wherein generating the at least one anatomical association for the first image is based on the gaze location data and the image position data.

8. The computer-implemented method of claim 1 wherein generating the at least one anatomical association for the first image comprises:
   obtaining a plurality of candidate anatomical possibilities from a database; and
   determining the at least one anatomical association based on the plurality of candidate anatomical possibilities.

9. The computer-implemented method of claim 1 further comprising:
   applying a second trained machine learning model to at least one feature of a second image; and
   determining a second classification of the at least one feature of the second image based on the application of the second trained machine learning model to the at least one feature of the second image, wherein generating the at least one anatomical association for the first image is based on the second classification.

10. The computer-implemented method of claim 9 wherein the second image is a previously scanned image for a same patient.

11. A non-transitory computer readable medium storing instructions that, when executed by at least one processor, cause the at least one processor to perform operations comprising:
   receiving speech data from a dictation system;
   determining a clinical characterization based on the received speech data;
   receiving first image scan data for a first image;
   applying a feature extraction process to the received first image scan data to identify at least one feature of the first image;
   applying a trained machine learning model to the at least one feature of the first image, wherein the trained machine learning model is trained on historical anatomical associations generated for prior images;
   determining a first classification of the at least one feature in the first image based on the application of the trained machine learning model to the at least one feature of the first image;
   generating at least one anatomical association for the first image based on the first classification and the clinical characterization; and
   providing the at least one anatomical association for display.

12. The non-transitory computer readable medium of claim 11 storing instructions that, when executed by at least one processor, further cause the at least one processor to perform operations comprising:
   applying a second trained machine learning model to at least one feature of a second image; and
   determining a second classification of the at least one feature of the second image based on the application of the second trained machine learning model to the at least one feature of the second image, wherein generating the at least one anatomical association for the first image is based on the second classification.

13. The non-transitory computer readable medium of claim 12 wherein the second image is a previously scanned image for a same patient.

14. A system comprising:
   a database; and
   at least one processor communicatively coupled to the database and configured to:
   receive speech data from a dictation system;
   determine a clinical characterization based on the received speech data;
   obtain first image scan data for a first image from the database;
   apply a feature extraction process to the received first image scan data to identify at least one feature of the first image;
   apply a trained machine learning model to the at least one feature of the first image, wherein the trained machine learning model is trained on historical anatomical associations generated for prior images;

determine a first classification of the at least one feature in the first image based on the application of the trained machine learning model to the at least one feature of the first image;

generate at least one anatomical association for the first image based on the first classification and the clinical characterization; and provide the at least one anatomical association for display.

15. The system of claim 14, wherein the at least one processor is configured to:

receive gaze location data from an eye tracking system, wherein the gaze location data identifies a position of an eye of a technician viewing the first image; and receive image position data from an image display system, wherein the image position data identifies a position of the first image being viewed by the technician, wherein generating the at least one anatomical association for the first image is based on the gaze location data and the image position data.

16. The system of claim 14, wherein the at least one processor is configured to:

apply a second trained machine learning model to at least one feature of a second image; and determine a second classification of the at least one feature of the second image based on the application of the second trained machine learning model to the at least one feature of the second image, wherein generating the at least one anatomical association for the first image is based on the second classification.

17. The system of claim 16, wherein the second image is a previously scanned image for a same patient.

18. The system of claim 14, wherein the at least one processor is configured to determine the clinical characterization based on applying a natural language process to the received speech data.

19. The system of claim 14, wherein the trained machine learning model is based on a convolutional neuronal network.

20. The system of claim 14, wherein the at least one processor is configured to determine a clinical indication based on the received speech data, wherein generating the at least one anatomical association for the first image is based on the clinical indication.

* * * * *